(12) United States Patent
Yan

(10) Patent No.: US 6,569,325 B1
(45) Date of Patent: May 27, 2003

(54) MULTIUSE PRESSURE ELECTRIC CHROMATOGRAPHIC DEVICE

(76) Inventor: Chao Yan, 4713 First St., Suite 225, Pleasanton, CA (US) 94566

(*) Notice: Subject to any disclaimer, the term of this patent is extended or adjusted under 35 U.S.C. 154(b) by 0 days.

(21) Appl. No.: 09/914,194

(22) PCT Filed: Mar. 20, 2000

(86) PCT No.: PCT/CN00/00055

§ 371 (c)(1),
(2), (4) Date: Aug. 22, 2001

(87) PCT Pub. No.: WO00/57172

PCT Pub. Date: Sep. 28, 2000

(30) Foreign Application Priority Data

Mar. 23, 1999 (CN) ........................ 99206093 U

(51) Int. Cl.⁷ ............................................... B01D 15/08
(52) U.S. Cl. ................... 210/198.2; 210/656; 204/453; 204/604
(58) Field of Search ................. 210/635, 656, 210/659, 748, 198.2, 243; 204/453, 604; 73/61.56

(56) References Cited

U.S. PATENT DOCUMENTS

| 3,997,298 A | * 12/1976 | McLaffertt ............... 210/198.2 |
|---|---|---|
| 4,632,762 A | * 12/1986 | Ramsland ................ 210/198.2 |
| 4,708,782 A | * 11/1987 | Andresen ................ 210/198.2 |
| 5,217,590 A | * 6/1993 | Lauer ........................ 204/604 |
| 5,246,577 A | * 9/1993 | Fuchs ...................... 210/198.2 |
| 5,310,463 A | * 5/1994 | Dadoo ..................... 210/198.2 |
| 5,646,048 A | * 7/1997 | Templin .................. 210/198.2 |
| 5,935,522 A | * 8/1999 | Swerdlow ............... 210/198.2 |
| 6,136,187 A | * 10/2000 | Zare ....................... 210/198.2 |

FOREIGN PATENT DOCUMENTS

| EP | 0 600 213 | 6/1996 | ............. 210/198.2 |
|---|---|---|---|
| WO | WO97/18579 | 5/1997 | ............. 210/198.2 |

* cited by examiner

Primary Examiner—Ernest G. Therkorn
(74) Attorney, Agent, or Firm—Intellectual Property Law Group LLP; Otto O. Lee; Juneko C. Jackson

(57) ABSTRACT

The present invention is a separation-detection device, which comprises high-voltage power supply, capillary chromatographic column and detection equipment. In addition, the present invention employs high-pressure pump. The device can apply pressure forward, backward or bi-directionally on the capillary column and rinse the column forward or backward with the high-pressure pump. Thus not only avoid bubble formation and current breakdown in column but also guarantee the high efficiency. It can run in several modes by changing different chromatographic columns.

6 Claims, 1 Drawing Sheet

MULTIUSE PRESSURE ELECTRIC CHROMATOGRAPHIC DEVICE

REFERENCE TO RELATED APPLICATIONS

This application is a 371 of PCT/CN00/00055 filed Mar. 20, 2000.

BACKGROUND

The present invention is a separation-detection device related to separation and analysis, namely a multifuctional pressurized electrochromatography system.

Most of the separation-detection devices comprise a mobile phase driving system, a chromatographic column and a detection instrument. Several familiar instruments are mentioned below:

1. Gas chromatography, which comprises a gas supply, a gas chromatographic column and a detector, is mainly used to separate gas mixture or low-boiling-point substances.
2. Liquid chromatography, which comprises a high-pressure pump, a steel chromatographic column with packing materials and a detector, is mainly used to separate liquid mixture. Liquid chromatography has a good selectivity. But the flow of mobile phase is driven by pressure rather than by electric field. The parabolic flow profile and band broadening obtained causes low column efficiency.
3. Capillary electrophoresis, comprises a high-voltage power supply, an empty capillary and a detector. Higher efficiency can be generated because of its plug-like flow driven by electro-osmotic flow. But its selectivity to neutral substances is poor.
4. Capillary electrochromatography comprises a high-voltage power supply, a capillary chromatographic column with a packing material and a detector. Capillary electrochromatography combines the high selectivity of liquid chromatography with the high efficiencies of capillary electrophoresis. But the presence of bubble formation within the column frequently leads to the breakdown of current in practice.

SUMMARY OF INVENTION

The objective of the present invention is to develop state of the art separation-detection equipment, which can not only provide high efficiency and high selectivity, but also remove the bubble continually to avoid the breakdown of current and rinse out the electrolytic products.

Above-mentioned objective is implemented by an equipment comprising a driving device, a chromatographic column and a detection system, while its driving device includes one or more high-pressure pump and one more high-voltage power supply.

A pipe connected with the inlet of said high-pressure pump is inserted in mobile phase. The outlets of high-pressure pump are connected with two capillaries. Capillary 18 goes through check valve 9 and its end is connected with the tail end of a column and a resistant column with check valve 20. Capillary 17 goes through check valves 8 and 13. It is connected with an injector with a capillary at a point between check valve 8 and 13. The injector is connected with the front end of the chromatographic column.

Number of said pump is one or more.

Said chromatographic column can be a capillary with packing materials.

Said chromatographic column can be an empty capillary.

Said chromatographic column can be a steel chromatographic column with packing materials.

Above-mentioned separation-detection equipment can apply pressure forwardly, backwardly or bi-directionally. It can not only assures that there is bubble formation in the column while avoiding the breakdown of current, but also rinse the column forward or backward. By applying equal pressure on both ends of the column, it is assured that the flow of mobile phase is only driven by electric field. Therefore, the high efficiency of electrochromatography is guaranteed. This present instrument can replace capillary electrochromatography equipment, capillary electrophoresis equipment and liquid chromatography equipment by changing different columns. Its performance is much improved over the existing equipments.

BRIEF DESCRIPTION OF THE DRAWINGS

FIG. 1 includes: mobile phase 1, mobile phase 2, pump 3, pump 4, tee 5, tee 6, fixture 7, check valve 8, check valve 9, injector 10, tee 11, column 12, check valve 13, high-voltage power supply 14, detector 15, detection cell 16, capillary 17, capillary 18, tee 19, check valve 20, resistant column 21, computer 22.

DETAILED DESCRIPTION OF THE INVENTION

Figure 1:
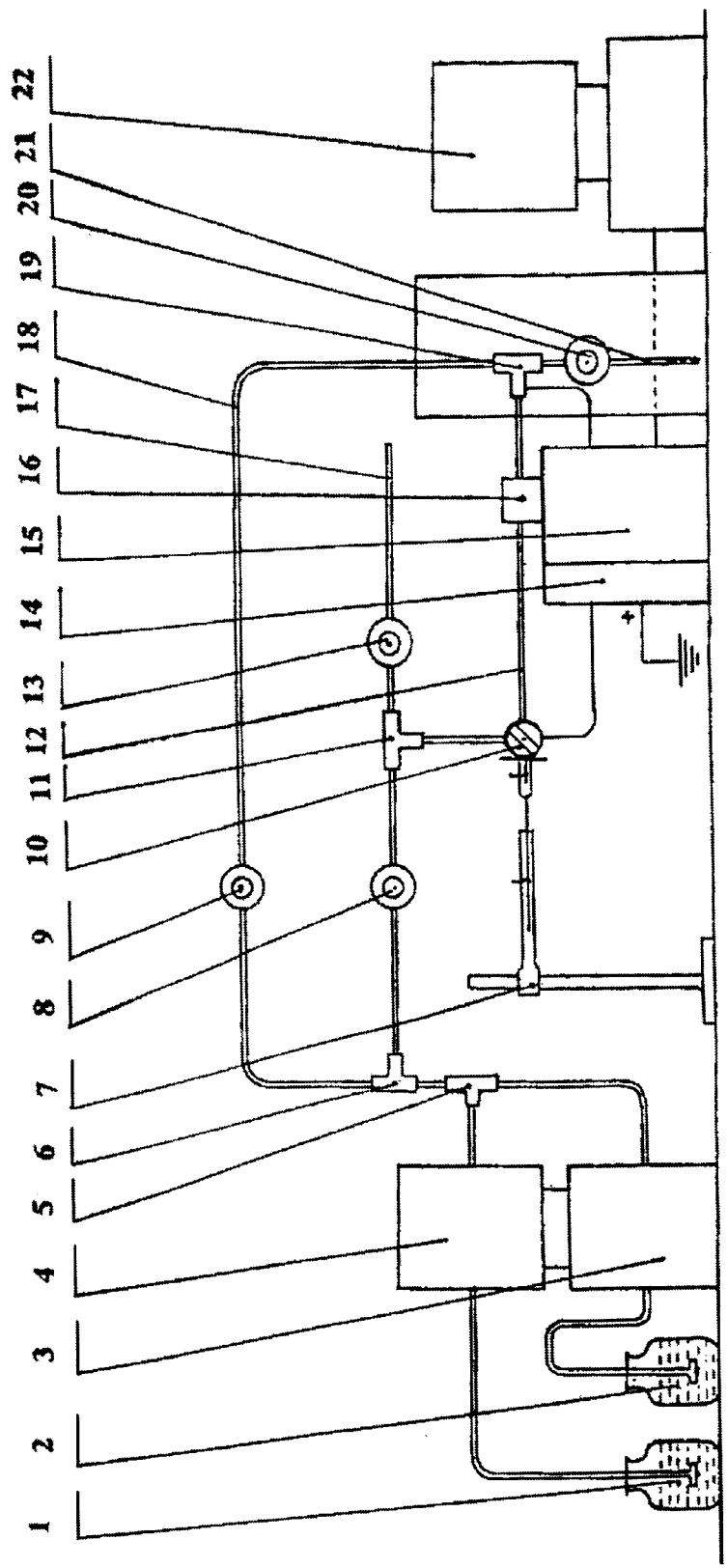
FIG. 1 is a schematic diagram of an embodiment of the present invention. The equipment comprises mobile phase 1, mobile phase 2, pump 3, pump 4, tee 5, tee 6, fixture 7, check valve 8, check valve 9, injector 10, tee 11, column 12, check valve 13, high-voltage power supply 14, detector 15, detection cell 16, capillary 17, capillary 18, tee 19, check valve 20, resistant column 21, computer 22.

Herein we will illustrate an embodiment of the present invention according to FIG. 1.

A pipe connected with the inlet of pump 3 is inserted into mobile phase 2. A pipe connected with the inlet of pump 4 is inserted into mobile phase 1. The outlets of pump 3 and pump 4 are connected to tee 5. The rest port of tee 5 is connected with tee 6. Capillary 17 and 18 are connected to the two rest ports of tee 6. Capillary 17 is connected with tee 11 through check valve 8. The end of capillary 17 passes through check valve 13 and is exposed in air. The rest port of tee 11 is connected with injector 10 by tubing. One of the three rest ports is connected with column, one for injection and the other for accepting excrescent sample liquid. Capillary 18 is connected with tee 19 through check valve 9. One port of tee 19 is connected with the end of column 12. One port of tee 19 is connected with resistant column 21. There is a check valve 20 on resistant column 21. The ground of negative high-voltage power supply is connected to metallic injector 10 and cathode to metallic tee 19. The detection window at the rear of column 12 is adjusted to fit the optical route. Detector 15 is connected with computer 22. Forward, backward and bidirectional pressurization can be implemented by adjusting the check valves. Forward and backward rinse is also achievable.

EXAMPLES

1. Pressurized Electrochromatography Mode

A 200 mm (400 mm total )×320 $\mu$m I.D. (630 $\mu$m O.D.) column, packed with 3 $\mu$m ODS stationary phase was employed for all the experimental work. The sample was a mixture of thiourea, benzyl alcohol and naphthalene.

Mobile phase 1 was 75% ethanol. Mobile phase 2 was the mixer of 70% acetonitrile and 30% 4 mM borax. We closed check valve 9 and 13 and open check valve 8 and 20. We then turned on pump 3, rinse and condition capillary column with mobile phase 2. Then we closed check valve 13, and opened the check valves 9, 8 and 20. We applied pressure to both ends of the capillary column. Remark: Because the resistant column 21 was made by packed capillary or open capillary, its restrictive effect to the flow was comparatively strong. So opening check valve 20 not only recycled the liquid at the column end, but also had no effect on applying pressure on both ends. Then high voltage might be applied on both ends of the capillary column and checked the current and its stability. If the current stayed constant, we opened the detection system and prepared for the detection. First we injected a sample into the 20 nl inject valve through the injection port by an injector, then injected the sample by twisting the knob. We turned off the high-voltage power supply before injection. After injection, we immediately applied the high voltage by turning on the power supply. Several minutes later, we could observe the three peaks of samples. We repeated the experiment three times to testify the reliability. After finishing the experiment, we powered off pump 3 and turned on pump 4. We closed check valve 9 and 13 and opened check valve 8 and 20. We rinsed the capillary column with mobile phase 1. If the capillary column was blocked, we might rinse the column backward, i.e., close check valve 8 and 20 and open check valve 9 and 13.

2. Capillary Electrophoresis Mode

Rreplaceing the column with an empty capillary, the present instrument is an art-of-the-date capillary electrophoresis equipment. Compared to a traditional capillary electrophoresis equipment, the present instrument implements injection by a quantitative injector rather than dip-in method. This equipment can also pressurize and rinse forward, backward or bi-directionally, and performance excels the traditional capillary electrophoresis equipment.

3. Micro-liquid Chromatography Mode

We turned off the high-voltage power supply and drove the mobile phase by pump only. We closed check valve 9 and 13, and opened check valve 8 and 20. We adjusted resistant column 21 and made it unobstructed. The present instrument can work as a micro-liquid chromatography equipment when using a capillary chromatographic column or a steel chromatographic column with packing materials. The present instrument works as a conventional micro-liquid chromatography equipment when using one pump. When two or more pumps are employed, the present instrument can carry out micro-gradient liquid chromatography. Because of its capability of rinsing forward and backward, the present invention is easy to control.

What is claimed is:

1. A separation-detection device, which comprises:
  a) a mobile phase driving device,
  b) a chromatography column,
  c) a detector,
     wherein said driving device comprises at least one high-pressure pump and a high-voltage power supply,
  d) a pipe connected with an inlet of said high-pressure pump being inserted in said mobile phase driving device.
  e) one or more outlets of said high-pressure pump being connected with a first capillary and a second capillary, said second capillary passing through a first check valve, and one end of said second capillary being connected with a tail end of a column and a resistant column via a second check valve,
  f) said first capillary passing through a third check valve and a fourth check valve, said first capillary being connected with an injector with a capillary at a point between said third check valve and said fourth check valve, said injector being connected with a front end of said chromatographic column.

2. The separation-detection device of claim 1 having more than one of said high-pressure pump.

3. The separation-detection device of claim 1, wherein said chromatographic column is a capillary column with a packing material.

4. The separation-detection device of claim 1, wherein said chromatographic column is an empty capillary.

5. The separation-detection device of claim 1, wherein said chromatographic column is a steel chromatographic column.

6. The separation-detection device of claim 5, wherein the steel chromatographic column includes one or more packing materials.

* * * * *